United States Patent [19]

Matheny et al.

[11] Patent Number: 5,651,378
[45] Date of Patent: Jul. 29, 1997

[54] METHOD OF USING VAGAL NERVE STIMULATION IN SURGERY

[75] Inventors: Robert G. Matheny, Carmel, Ind.; Charles S. Taylor, San Francisco, Calif.

[73] Assignee: Cardiothoracic Systems, Inc., Portola Valley, Calif.

[21] Appl. No.: 603,411

[22] Filed: Feb. 20, 1996

[51] Int. Cl.$^6$ ........................................... A61B 19/00
[52] U.S. Cl. ........................ 128/898; 607/9; 607/10; 607/142
[58] Field of Search ........................ 128/898; 607/44, 607/14, 2, 15, 16, 121; 604/113, 53, 49

[56] References Cited

U.S. PATENT DOCUMENTS 5,330,507   7/1994   Schwartz .
5,458,625   10/1995  Kendall .

OTHER PUBLICATIONS

"Parasympathetic Control of the Heart," Walter C. Randall, Ph.D. Chapter 4, *Nervous Countrol of Cardiovascular Function*, (1984) pp. 68–94.

"Autonomic Control of Cardiac Pacemaker Activity and Atrioventricular Transmission," M. Levy and H. Zieske *Journal of Applied Physiology*, vol. 27, No. 4, Oct. 1969.

"Adenosine: Electrophysiologic Effects and Therapeutic Use for Terminating Paroxysmal Supraventricular Tachycardia"., J.P. DiMarco, M.D.; T.D. Sellers, M.D.; R.M. Berne, M.D.; G.A. West, B.S.; and L. Belardinelli, M.D. *Therapy and Prevention Arrhythmia*, Circulation 68, No. 6, 1254–1263, 1983.

"Safety of Different Dosages of Intravenous Adenosine Used in Cojunction with Diagnostic Myocardial Imaging Techniques," S.M. Mohiuddin, M.D.; D.J. Esterbrooks, M.D.; N.C. Gupta, M.D.; and D.E. Hilleman, Pharm.D. *Pharmacotherapy* 1993, 13(5), pp. 476–480.

"Adenosine and Its Cardiovascular Effects," A.Freilich, M.D. and D. Tepper, M.D. *Amercian Heart Journal*, vol. 123, No. 5, (May, 1992), pp. 1324–1328.

Benetti, FJ "Direct coronary artery surgery with sahenous vein bypass without either cardiopulmonary by pass or cardiac arrest." J. Cardiovasc. Surg. 26:217–22. 1985.

Benetti, et al. "Use of thoracoscopy and a minimal thoracotomy, in mammary–coronary bypass to left anterior descending artery, without extracorpoeal circulation." J. Cardiovac. Surg.;36:159–61 Apr. 1995.

Westaby, S. "Coronary surgery without cardopulmonary bypass." British Heart Journal; 73:203–205 1995.

*Primary Examiner*—Aaron J. Lewis
*Assistant Examiner*—Kelly Riskin O'Hara
*Attorney, Agent, or Firm*—Lyon & Lyon LLP

[57] ABSTRACT

The invention comprises a method for facilitating coronary surgery on the beating heart wherein the vagal nerve is electrically stimulated to temporarily stop or substantially reduce the beating of the heart. Such temporary stoppage or substantial reduction of the beating of the heart facilitates procedures such as suturing of an anastomosis which would otherwise be more difficult because of the motion induced by the beating heart.

4 Claims, No Drawings

METHOD OF USING VAGAL NERVE STIMULATION IN SURGERY

BACKGROUND OF THE INVENTION

Coronary artery bypass graft (CABG) surgery has become a well known and conventional procedure, often referred to as "heart bypass" surgery. Such surgery is performed to relieve a condition in which a partially or fully blocked artery is no longer effective to transport blood to the heart and involves removing a portion of a vein from another part of the body, frequently the saphenous vein, to use as a graft and installing this graft at points at which bypass the obstruction to restore normal blood flow to the heart. Common though this procedure has become, it is nevertheless lengthy, traumatic and subject to patient risk. Among the risk factors involved is the use of cardiopulmonary bypass equipment, i.e., the so-called "heart-lung machine", to both pump blood and oxygenate the blood so that the patient's heart may be stopped during the surgery, with its function performed by the cardiopulmonary bypass equipment.

Prior to the present invention, it has been found possible to conduct CABG surgery without stopping the heart, i.e., on a beating heart. In such a beating heart procedure, the function of the heart is maintained and the cardiopulmonary bypass equipment is not needed to replace that function. However, since the heart is beating in such a procedure, the surgeon must cope with the movement of the heart, whether the surgery is a bypass procedure or any other type of coronary surgery. The present invention addresses this problem.

The performance of coronary surgery on the beating heart is described by Benetti et al in "Coronary Revascularization With Arterial Conduits Via a Small Thoracotomy and Assisted by Thoracoscopy, Although Without Cardiopulmonary Bypass", Cor. Europatum, 4(1):22–24 (1995), which is incorporated herein by reference and by Westaby, "Coronary Surgery Without Cardiopulmonary Bypass" in the March, 1995 issue of the British Heart Journal which is incorporated by reference herein. Additional discussion of this subject matter can be found in Benetti et al, Chest, 100(2):312–16 (1991), Pfister et al, Ann. Thorac. Surg., 54:1085–92 (1992), and Fanning et al, Ann. Thorac. Surg., 55:486–89 (1993). These articles discuss the further details of grafting by anastomosis of a saphenous vein or mammary artery to diseased coronary arteries including the LAD or the right coronary artery (RCA), temporary occlusion of the coronary artery to provide a bloodless anastomotic field, use of a double suture placed above and below the point of anastomosis, and use of a running suture for the anastomosis. These articles also contrast the beating heart procedure to the more widely used CABG method performed on the non-beating heart with cardiopulmonary bypass.

SUMMARY OF THE INVENTION

In heart surgery performed while heart is beating, surgeon is faced with a moving organ which places increased demands on his skill in performing the desired procedure, e.g., an anastomosis of the left anterior descending artery (LAD) to the left internal mammary artery (LIMA) or anastomoses of both ends of a free graft means to a target artery and a coronary artery. If, without substantial harm to the patient, the heart could be momentarily substantially stopped or slowed while the surgeon performed the desired task, e.g., taking a stitch with a suturing needle, such task would be less difficult to accomplish.

The purpose of the present invention is to provide a surgical procedure in which the heart is momentarily substantially stopped or slowed in a predictable and reliable manner to facilitate the surgery by electrically stimulating the vagus nerve. This stimulation can be accomplished by gaining access to the vagus nerve in the neck or in the chest and then using a suitable device, e.g., a commercially available nerve stimulator or insulated pacing wires with distally exposed conductors connected to a current source, to briefly, e.g., for 1 to 5 seconds, apply electric energy to the vagus nerve. A 50 millihertz current may be used, but the present invention is not limited to any particular quantitative amount of electrical energy.

The time of the stimulation and amount of current applied will vary according to the type of surgery and the nature of the task for which substantial stopping or slowing of the heart is desired. In any event, the normal sinuous rhythm of the heart is rapidly restored by natural forces once the stimulation is terminated. Thus, for repetitive tasks such as stitching during suturing, the stimulation may be repeatedly applied for brief intervals during which time the task can be performed in less difficult conditions than would apply if the heart were beating in a normal manner.

The role of the vagus nerves in the control of cardiac rate and rhythm has been recognized for more than three centuries. Furthermore, soon after electrical stimulating devices became available, it was shown that vagal stimulation caused a reduction in heart rate and, as earlier as 1897, Hunt carried out a quantitative study of the effects of vagal stimulation on heart rate, Hunt, R., "Experiments on the Relation of the Inhibitory to the Accelerator Nerves of the Heart", J. Exp. Med. 2:252–279 (1897). An excellent discussions of this phenomenon is found in Chapter 4, Parasympathetic Control of the Heart, by Levy and Martin, in *Nervous Control of Cardiovascular Function*, edited by Randall, Oxford University Press (1984), which is incorporated by reference herein. However, in spite of the fact that the effect of vagal nerve stimulation on heart rate has long been known, it is believed that this knowledge has not previously been applied to coronary surgery. Rather, vagal nerve stimulation for other purposes has been employed, e.g., as disclosed in Schwartz U.S. Pat. No. 5,330,507 where vagal nerve stimulation is used in connection with treating arrhythmias and in Kendall U.S. Pat. No. 5,458,625 which addresses the use of vagal nerve stimulation for the alleviation of substance withdrawal symptoms or the provision of pain relief, stress relief, and/or general muscle relaxation. Thus, the present invention is believed to be the first use of vagal nerve stimulation to facilitate coronary surgery.

DETAILED DESCRIPTION OF THE INVENTION

The vagal nerve stimulation technique of the present invention may be used in open chest coronary surgery where a sternotomy is used to gain access to the heart or in closed chest beating heart coronary surgery in which a thoracotomy is used to gain access. The following is an exemplary usage of the latter procedure.

The patient is intubated with a double-lumen endobronchial tube which allows selective ventilation or deflation of the right and left lungs. The left lung is deflated to provide access to the heart and the LIMA. The preferred surgical position of the patient is right lateral decubitus, 30° from horizontal, with the left arm above the head.

Surgery begins with a left anterior thoracotomy over the fourth intercostal space. Other sites are suitable depending on the patient's physiology, particularly the fifth intercostal space. A retractor is used to spread the ribs to provide access to the beating heart. The size of the thoracotomy varies depending on the patient, but generally is less than 12 cm. The parietal pleura is dissected and separated from the ribbons, to permit the introduction of a thoroscope through a procar at the fourth intercostal space, medial axillary line. The thoroscope may be introduced through other areas such as the fifth through seventh intercostal spaces, again depending on the patient's physiology. The thoroscope is positioned to provide visualization of the LIMA. The LIMA is then dissected with suitable instruments introduced through the thoracotomy. These instruments generally comprise scissors, clippers, pliers, electrocauteries or other conventional devices useful for the dissection. It is sometimes useful to make a graft with a radial artery coming out from the LIMA in a T-form. This allows formation of anastomoses with multiple coronary arteries such as sequential grafts to the Dx and Cx arteries.

Following dissection of the LIMA, a small pericardial incision is made to expose the LAD. Access to the LAD and Dx arteries is typically relatively easy, requiring an incision of about 5 cm. Access to the Cx artery depends on the patient's characteristics and location of the vessels. In some cases, a graft to the Cx artery requires increased rotation of the patient to the right lateral decubitus and some extension of the pericardial incision. Heparin, or other suitable anticoagulant, may be administered to the patient in an appropriate dose such as 1.5 mg/kg.

To prevent excess bleeding and partially stabilize the vessel, a segment of LAD is occluded with ligating stay sutures comprising 2.5 cm lengths of 5/0 polypropylene or other appropriate ligature material. Applying tension to the ligatures helps stabilize the LAD even though the heart is beating. Other conventional means for occluding and stabilizing the artery may be suitable as well. Furthermore, forceps are also introduced through the thoracotomy so further stabilize and retract the LAD. A scalpel is then introduced to perform an arteriotomy in the LAD.

An anastomosis between the LIMA and the LAD is then performed by suturing with 7/0 polypropylene using a needle manipulated by a forceps.

It is at this point that vagal nerve stimulation is used to temporarily stop or slow the heart to reduce motion in the anastomosis field such that a suturing stitch is taken immediately after stimulation when the heart's motion is temporarily stopped or substantially reduced. The number of stitches required will, of course, dictate the number of occasions on which electrical stimulation of the vagal nerve will be desirable.

Upon completion of the anastomosis, the anticoagulant is reversed by suitable means such as protamine. The hemostasis should be carefully controlled. The thoracotomy is closed by conventional means. If the pleura is closed, a small tube for drainage may be left in place and removed the same day as the surgery. If the pleura is open, a larger tube should be left in place for 24 hours. All drainage tubes are introduced through the small incision for the thoroscope.

In the foregoing procedure, the electric stimulator, e.g., of the type disclosed in U.S. Pat. No. 5,458,625 and may be attached to the patient's ear, neck, or other points of access to the vagal nerve. The electrodes used to stimulate the vagal nerve may be non-invasive, e.g., clips, or invasive, e.g., needles. The electrical energy supplied to the vagal nerve will vary with the type of equipment used, the point in the body at which access to the vagal nerve is obtained, etc. and it is to be understood that the practice of the present invention is not limited to any particular values. Rather, the appropriate amount of electrical energy needed to achieve the desired result can be readily determined empirically once the type of equipment, point of access, etc. are known.

The present invention is not limited to the scope of the foregoing detailed description, but is of the full scope of the claims appended hereto.

We claim:

1. A method for performing coronary artery bypass graft surgery on a patient's beating heart comprising the steps of:

forming at least one opening in the patient's chest;

locating a target artery for an arterial blood supply;

dissecting said target artery in preparation for fluid connection to a portion of a coronary artery distal from a stenosis;

connecting said target artery in fluid communication with said coronary artery; and electrically stimulating the patient's vagal nerve at least once during said connecting step to temporarily stop or substantially reduce the beating of the patient's heart.

2. The method of claim 1 wherein the step of connecting the target artery in fluid communication with the coronary artery comprises forming an anastomosis between the target artery and the coronary artery.

3. The method of claim 1 wherein the step of connecting the target artery in fluid communication with the coronary artery comprises supplying a free graft means having first and second ends, forming a first anastomosis between the first end of the graft means and the target artery and forming a second anastomosis between the second end of the graft means and the coronary artery.

4. The method of claim 1 wherein said connecting step comprises a series of suturing steps and in which the vagal nerve is stimulated before at least one suturing step.

* * * * *